(12) United States Patent
Bolser (10) Patent No.: US 6,602,188 B2
(45) Date of Patent: Aug. 5, 2003

(54) SURGICAL INSTRUMENT AND ASSOCIATED METHOD

(76) Inventor: Jeffrey William Bolser, 478 Carol Dr., Vadnais Heights, MN (US) 55127

(*) Notice: Subject to any disclaimer, the term of this patent is extended or adjusted under 35 U.S.C. 154(b) by 4 days.

(21) Appl. No.: 09/794,315

(22) Filed: Feb. 22, 2001

(65) Prior Publication Data

US 2002/0115909 A1 Aug. 22, 2002

(51) Int. Cl.[7] .................................................. A61B 1/32
(52) U.S. Cl. ........................ 600/210; 600/199; 600/245; 600/235
(58) Field of Search .................................. 600/210, 212, 600/213–215, 234, 235, 242, 245, 201, 199, 241

(56) References Cited

U.S. PATENT DOCUMENTS

| 4,052,980 A | * | 10/1977 | Grams et al. ................ 600/201 |
| 5,921,919 A | * | 7/1999 | Chin et al. ................... 600/217 |
| 5,967,971 A | * | 10/1999 | Bolser ......................... 600/211 |
| 6,228,025 B1 | * | 5/2001 | Hipps et al. ................. 600/213 |

* cited by examiner

Primary Examiner—Kevin Shaver
Assistant Examiner—Michael B. Priddy
(74) Attorney, Agent, or Firm—Beck & Tysver, P.L.L.C.

(57) ABSTRACT

An surgical instrument for use during procedures to harvest saphenous veins simultaneously retracts tissue and exposes sections of the vein. Removable spacer limbs are selectively attached to the instrument to aid in retracting tissue and to make the instrument self-retaining.

18 Claims, 8 Drawing Sheets

SURGICAL INSTRUMENT AND ASSOCIATED METHOD

FIELD OF THE INVENTION

The present invention relates generally to surgical instruments and more particularly to a surgical retractor well suited to harvesting saphenous veins for use in coronary bypass operations.

BACKGROUND OF THE INVENTION

Harvesting segments of the saphenous vein from the leg is a surgical procedure associated with coronary artery surgery. In general, segments of the patient's saphenous vein are removed, divided and repositioned in the coronary arterial system to improve coronary blood flow.

Early harvesting techniques involved conventional surgical cut down and open dissection of the leg to harvest the vein. In general less invasive procedures are preferred and several surgical devices have been developed to facilitate this procedure. See for example the "Mini Harvest" system manufactured by U.S. Surgical Corp. and the "VasoView" system manufactured by Origin as well as U.S. Pat. No. 5,667,480 to Knight et al. In general these systems are relatively complex and cumbersome in use although they are preferred over open dissection.

SUMMARY OF THE INVENTION

In contrast to the prior art, the surgical retractor of the present invention is an easily manipulated illuminated device for insertion into the surgical wound to illuminate the surgical field. In use the device is manipulated by the physician and can be used to expose sections of the vein and it may be used to facilitate blunt dissection along the length of the vein. In operation the device can be used to simultaneously retract tissue and illuminate the surgical field at the same location. The illustrated embodiments of the device include a light source located near the distal tip of the retractor with an integral or remote power source of the light source.

BRIEF DESCRIPTION OF THE DRAWINGS

Throughout the several views of the drawing identical reference numerals refer to equivalent structural elements, wherein.

DETAILED DESCRIPTION

Figure 1:
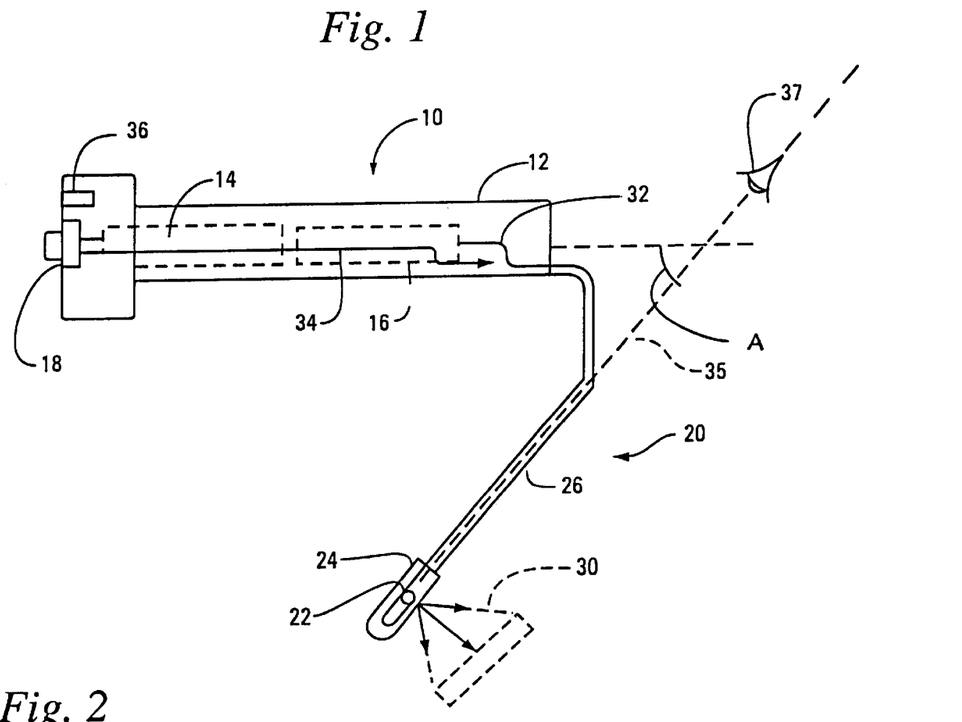
FIG. 1 is an illustrative view of an embodiment of a surgical instrument.

FIG. 1 shows a side view of an embodiment of the surgical instrument 10. A handle 12 is provided to receive the hand of the physician. A power source is provided and is illustrated by a pair of batteries illustrated in the figure by battery 14 and battery 16 which may be located inside of the handle 12. In this embodiment the proximal end of the handle 12 includes a switch assembly 18 which can be used to turn on the light source 22 or lamp.

A retractor blade 20 is anchored at the distal end of the handle 12. In general this retractor blade lies in a single plane and bends "away" from the handle 12. Preferably, the blade attaches to the handle with a malleable construction, such that angle between the blade and the handle is adjustable to some degree by the user. Near the distal tip of the retractor blade 20 is a lamp 22 or other source of illumination. In the embodiment shown in the drawing a single incandescent bulb is shown mounted on a web 24 spanning the distance between the first limb 26 and the second limb 28 of the retractor blade 20. In general it is best to mount the bulb such that the cone of illumination 30 is directed away from the handle 12. In use this illumination source directs light into the surgical field surrounding and defined by the distal tip of the retractor blade.

Figure 2:
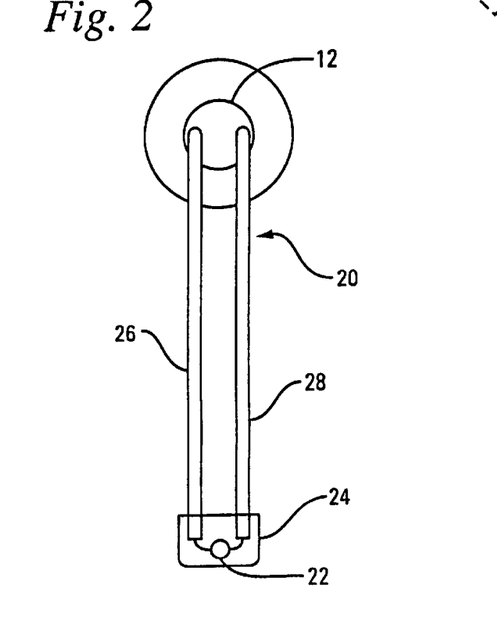
FIG. 2 is an illustrative view of the embodiment of a surgical instrument shown in FIG. 1.

FIG. 2 shows an end view of the surgical instrument 10. In this view the two members 26 and 28 can be seen forming conductors for the light source 22. The web 24 can be seen spanning the distance between the two members. In general the web 24 is formed from a plastic material and the web adds mechanical strength to support the two members 26 and 28. The circuit to the power source is completed by suitable wiring 32 which couples the member 26 conductor to a battery 16. A complimentary wire 34 couples member 28 to the switch assembly 18. The user with line of sight along line 35 from eye position 37 observes the surgical field between the two limbs 26 and limb 28. The line 35 forms an axis which lies in the plane generally defined by the two limb members 26 and 28.

FIGS. 3–6 illustrate embodiments of a surgical instrument that include a support or spacer arrangement which aids in holding open a tunnel through the tissue surrounding the saphenous vein for easily viewing the dissection area without having to hold and pull up on the surgical instrument at all times. In the embodiment of the surgical instrument 100 illustrated in FIGS. 3–5, the spacer arrangement is indicated at reference number 110; in the embodiment of the surgical instrument 200 illustrated in FIG. 6, the spacer arrangement is indicated at reference number 210.

Figure 3:
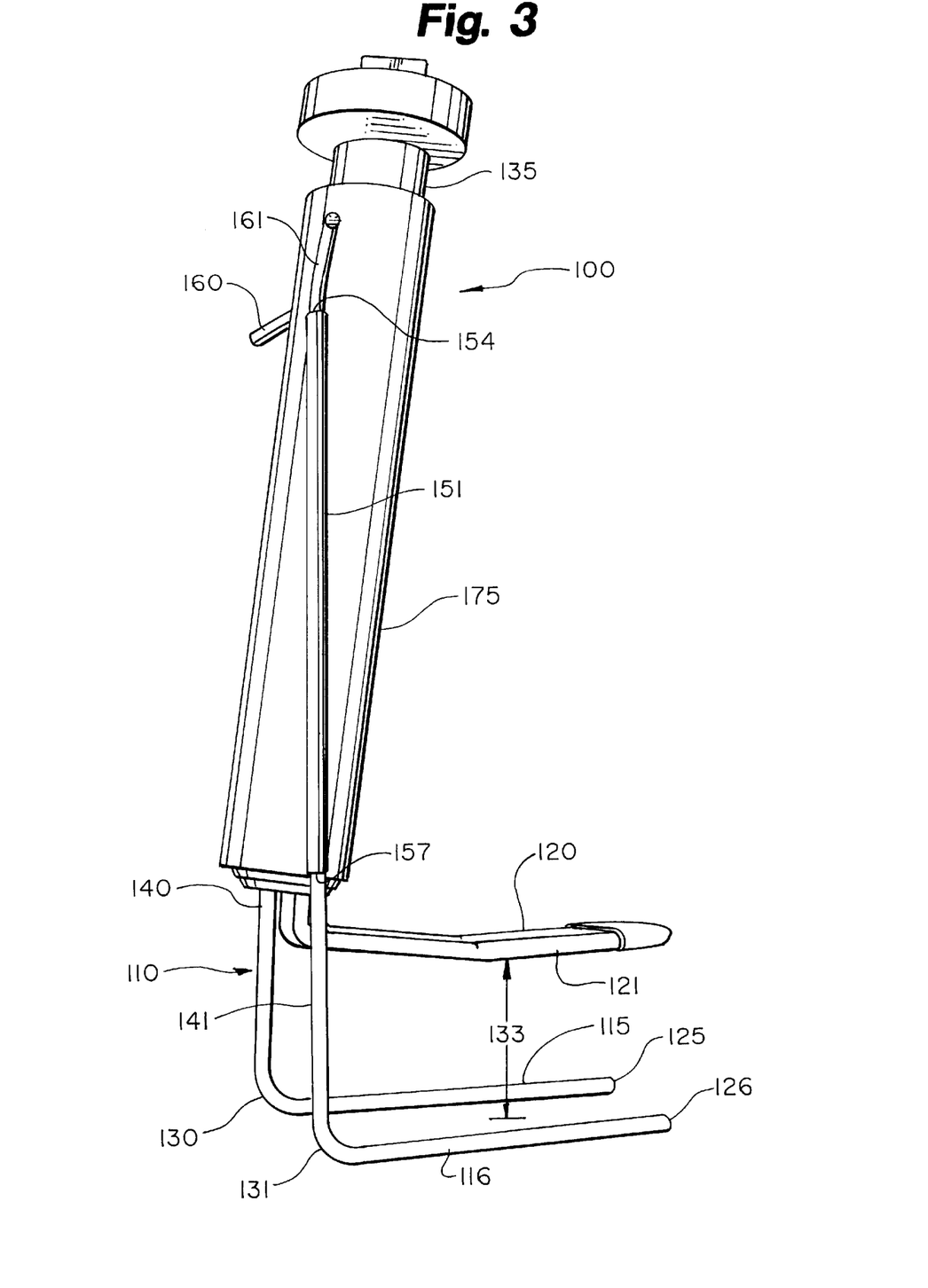
FIG. 3 is a perspective view, generally from the side, of another embodiment of a surgical instrument.
Figure 11:
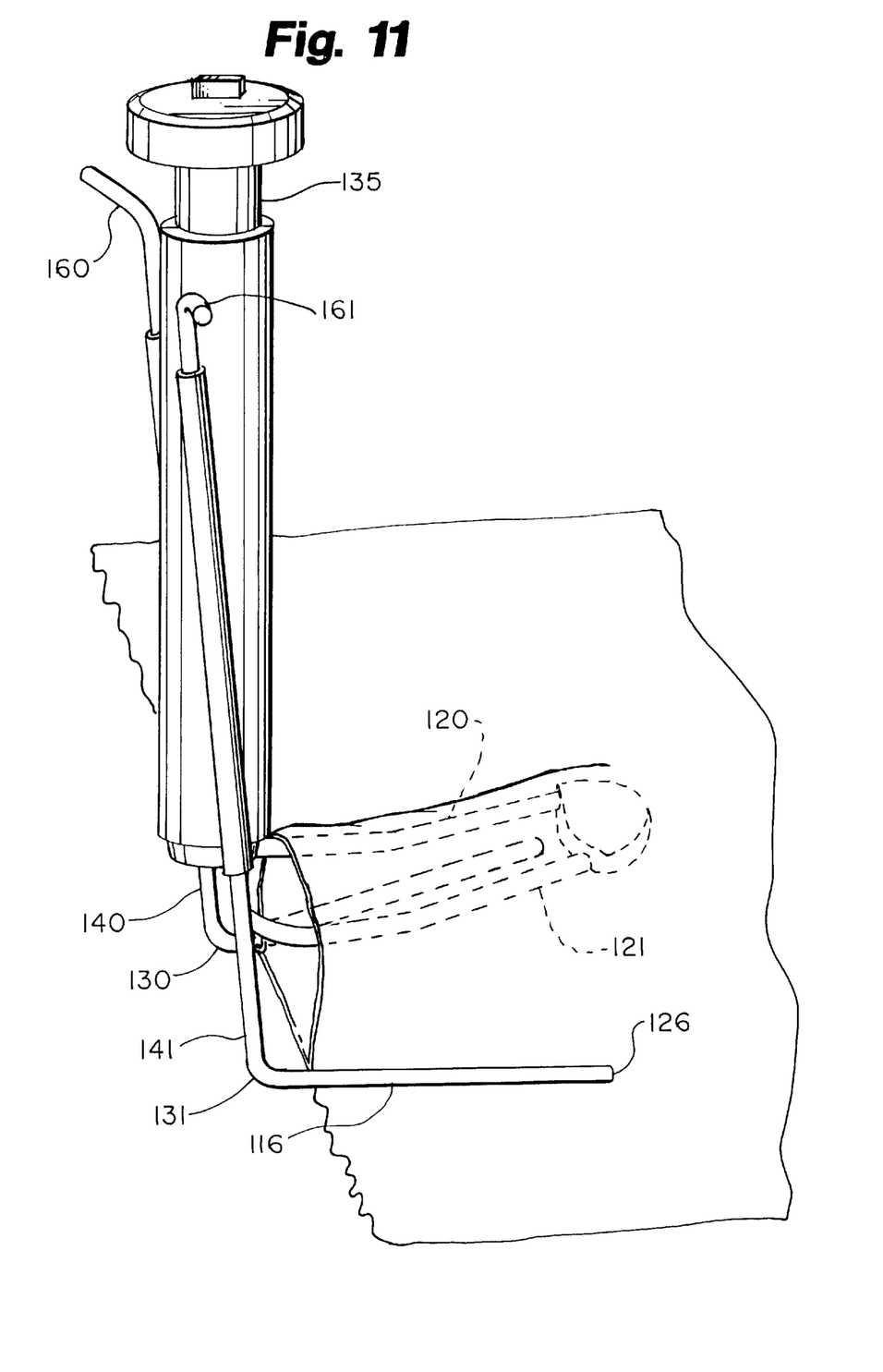
FIG. 11 is a perspective view, generally from the side, of a surgical instrument of FIG. 3 in use, with hidden portions under tissue indicated by dotted lines.

As illustrated in FIG. 3, the spacer arrangement 110 includes two spacer limbs 115 and 116. The spacer limbs 115 and 116 each extend generally parallel to the plane defined by limbs 120 and 121. Spacer limbs 115 and 116 are spaced apart from each other and are obliquely oriented in a preferred embodiment such that the terminating distal tips 125 and 126 are closer together than the opposite end portions 130, 131 of the limbs 115 and 116. The distal tips 125 and 126 may be connected or bridged or spanned to add mechanical strength. Alternatively, the orientation of disjoined spacer limbs to one another can be adjustable such that the spacer limbs can selectively be spread apart in a semi-V formation as illustrated in FIG. 11.

Preferably the distance 133 between the spacer limbs 115, 116 and the plane defined by limbs 120, 121 is variable between almost zero inches and about 2.5 inches. A relatively small distance will be used in operation when the device in introduced into an incision. The spacer limbs will then be extended to a distance of between about 1.0 inch and 2.5 inches to hold open a tunnel to facility the viewing of the surgical field. Preferably the spacer limbs 115, 116 can be locked or secured into a desired position relative to the limbs 120, 121 such that the instrument 100 supports a tunnel about the saphenous vein. This allows a clear view of and convenient access to the surgical field and even allows the user to let go of the instrument while the instrument maintains an open tunnel.

The spacer limbs 115, 116 illustrated in FIGS. 3–11 are generally circular in cross-section, though other shapes are contemplated. For example, the spacer limbs 115, 116 may be flattened with a rectangular or elliptical cross-section; alternatively, the spacer limbs 115, 116 may be generally circular in cross-section, but may include portions having flattened rectangular or elliptical cross-sections. The surfaces of the blade limbs 120, 121 and spacer limbs 115, 116 that engage tissue may be smooth or rough. Rough or ridged surfaces will provide increased frictional engagement between the tissue and the instrument.

A preferred embodiment includes two spacer limbs 115, 116; alternate embodiments are operable with one spacer limb or with more than two spacer limbs.

Figure 4:
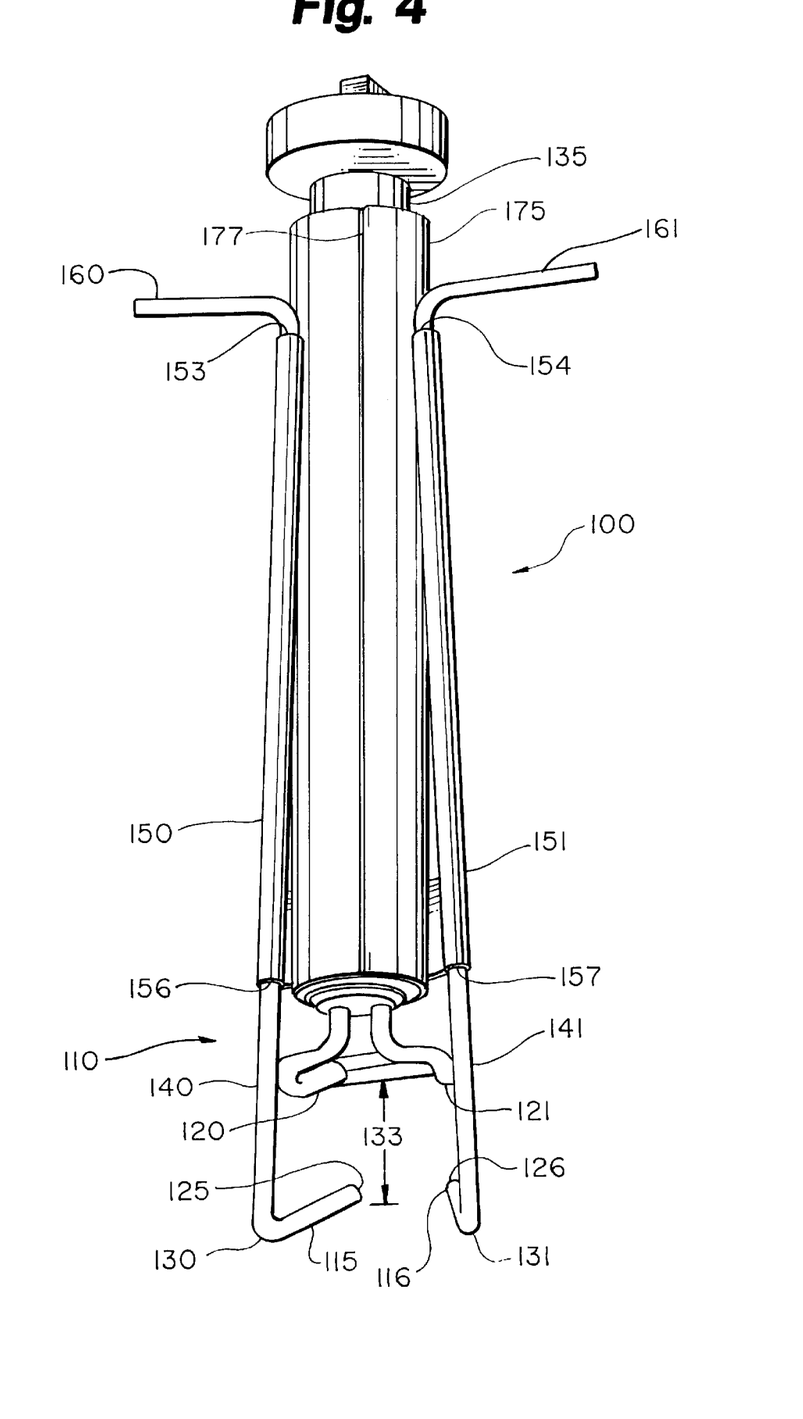
FIG. 4. is a perspective view, generally from the rear, of the surgical instrument illustrated in FIG. 3.

The spacer limbs 115, 116 can be coupled to the instrument in a number of ways. Preferably, as illustrated in FIG. 3, the spacer limbs 115, 116 are slidably coupled to the limbs 120 and 121 such that the distance between spacer limbs 115, 116 and the plane defined by limbs 120 and 121 is selectively variable. More specifically, as illustrated in the embodiment of FIGS. 3 and 4, the spacer limbs 115 and 116 are slidably coupled to the handle 135. Each spacer limb 115, 116 is integrally formed with an elongate member 140, 141, respectively, oriented generally perpendicular to the spacer limb 115, 116. This elongate member 140, 141 resides in a tube 150, 151 coupled to the handle 135. Tubes 150, 151 terminate in proximal ends 153, 154 and at distal ends 156, 157. Preferably, the elongate members 140, 141 are sized to slide in a longitudinal direction within the respective tube 150, 151. Flanges 160, 161 are integrally coupled to the proximal ends of the elongate member 140, 141 and are disposed generally perpendicular to the elongate member. The flanges 160, 161 limit the movement of the elongate member in the distal direction by abutting the proximal end 153, 154 of the tube 150, 151. The flanges further function as handles for the user to manipulate to adjust the longitudinal position of the spacer limbs 115, 116. In a preferred embodiment, the elongate members 140, 141 are independently moveable, such that spacer limbs 115, 116 can accordingly be separately or independently adjusted. In an alternate embodiment, member 140, 141 move in unison. The device can be constructed to allow the extension members to slide continuously through tubes 150, 151. Alternatively, the device can be constructed, for example with click stops, to provide one or more predefined preferred positions for the extension members to accommodate one or more predefined preferred distances between the spacer limbs and the plane defined by limbs 120 and 121.

Preferably, the spacer limbs 115, 116 are coupled to the blade limbs 120, 121 such that the angle defined between the spacer limbs and the blade limbs is adjustable, such as through malleability of the spacer limbs 115, 116, the extension members 140, 141 and/or the junction therebetween.

Figures 5A, 5B:
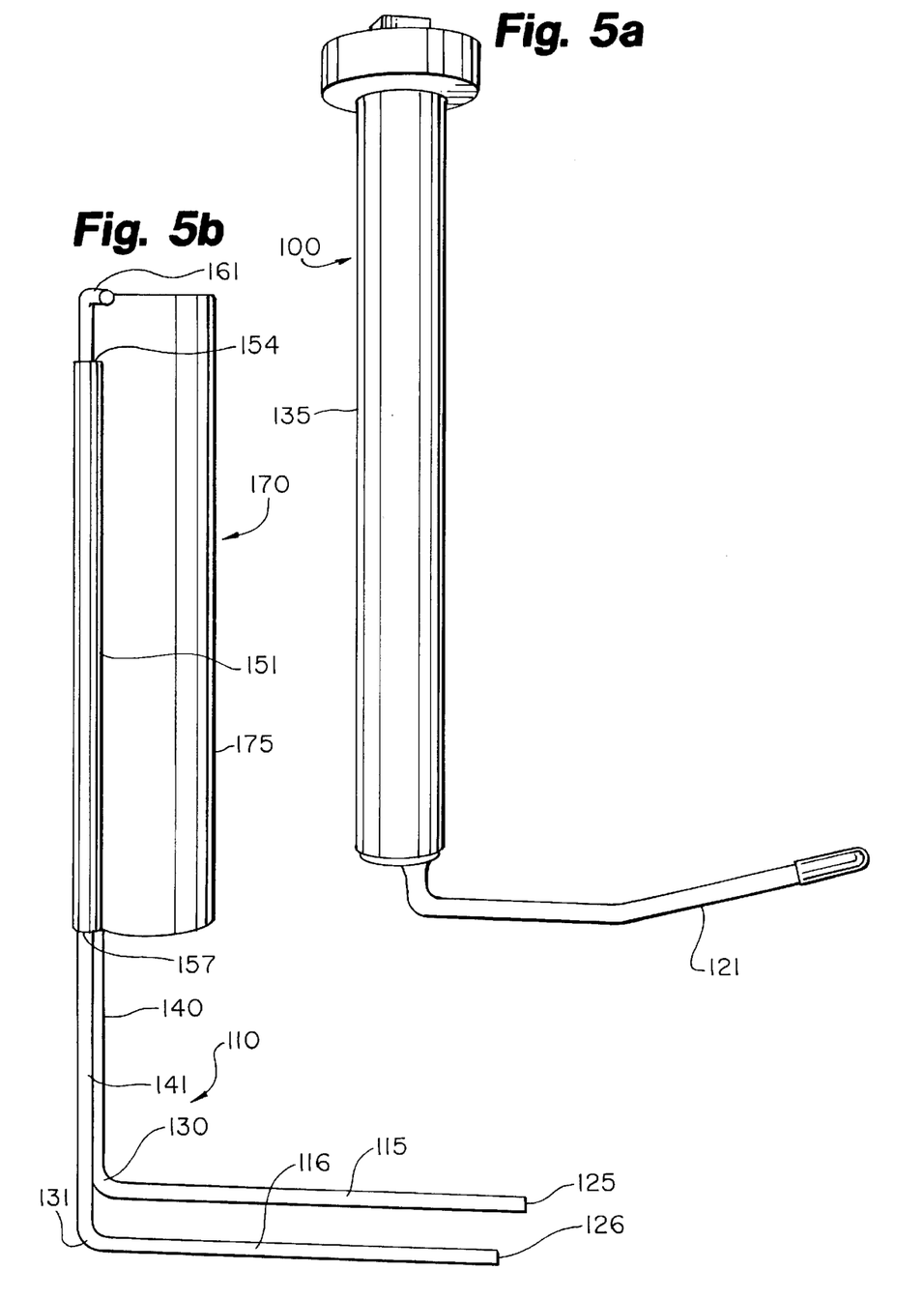
FIGS. 5a and 5b are perspective views, generally from the side, of the instrument shown in FIG. 3, with separable portions illustrated separately.

Additional arrangements for attaching the spacer limbs to the instrument are contemplated. For example, tubes 150, 151 can be fixed directly to the handle 135, such as by welding or gluing. Preferably, the tubes 150, 151, and therefore the limbs 115, 116, are removably coupled to the surgical instrument 100. As illustrated in FIGS. 5a and 5b, the spacer limbs 115, 116 are part of a spacer support assembly 170 which releasably attaches to the surgical instrument 100. In the embodiment illustrated in FIGS. 3–5, the spacer support assembly 170 includes a jacket 175 which attaches to the handle 135 by wrapping around it and clamping thereto. In one embodiment, illustrated in FIG. 9, the jacket 175 includes a living hinge 177 that opens for the jacket to receive the handle 135. Alternatively, the jacket 175 is made of a material, such as spring steel, that is resilient enough to allow the jacket to spread open to receive the handle, and then spring back to grip the handle 135. Other arrangements for attaching the jacket and/or the spacer limbs to the instrument 100 are contemplated. For example, the handle 135 can include notches, clips or the like to mate with corresponding structure on the jacket 175 or on tubes 150, 151.

Figures 6, 7, 8:
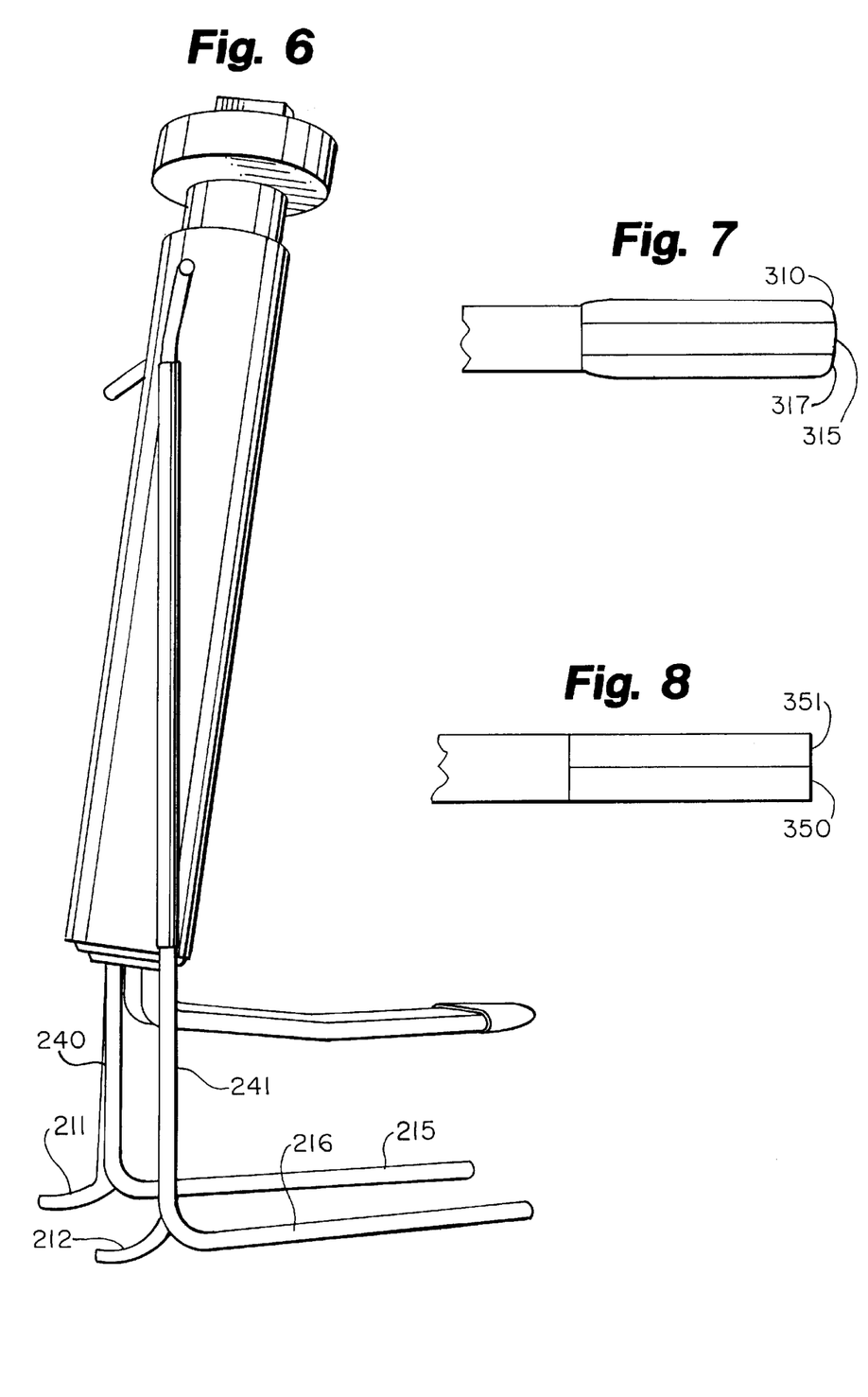
FIG. 6 is a perspective view, generally from the side, of an alternate embodiment of a surgical instrument.
FIG. 7 is an enlarged schematic side view of a portion of a surgical instrument according to the present invention.
FIG. 8 is an enlarged schematic side view of a portion of a surgical instrument according to the present invention.
Figure 9:
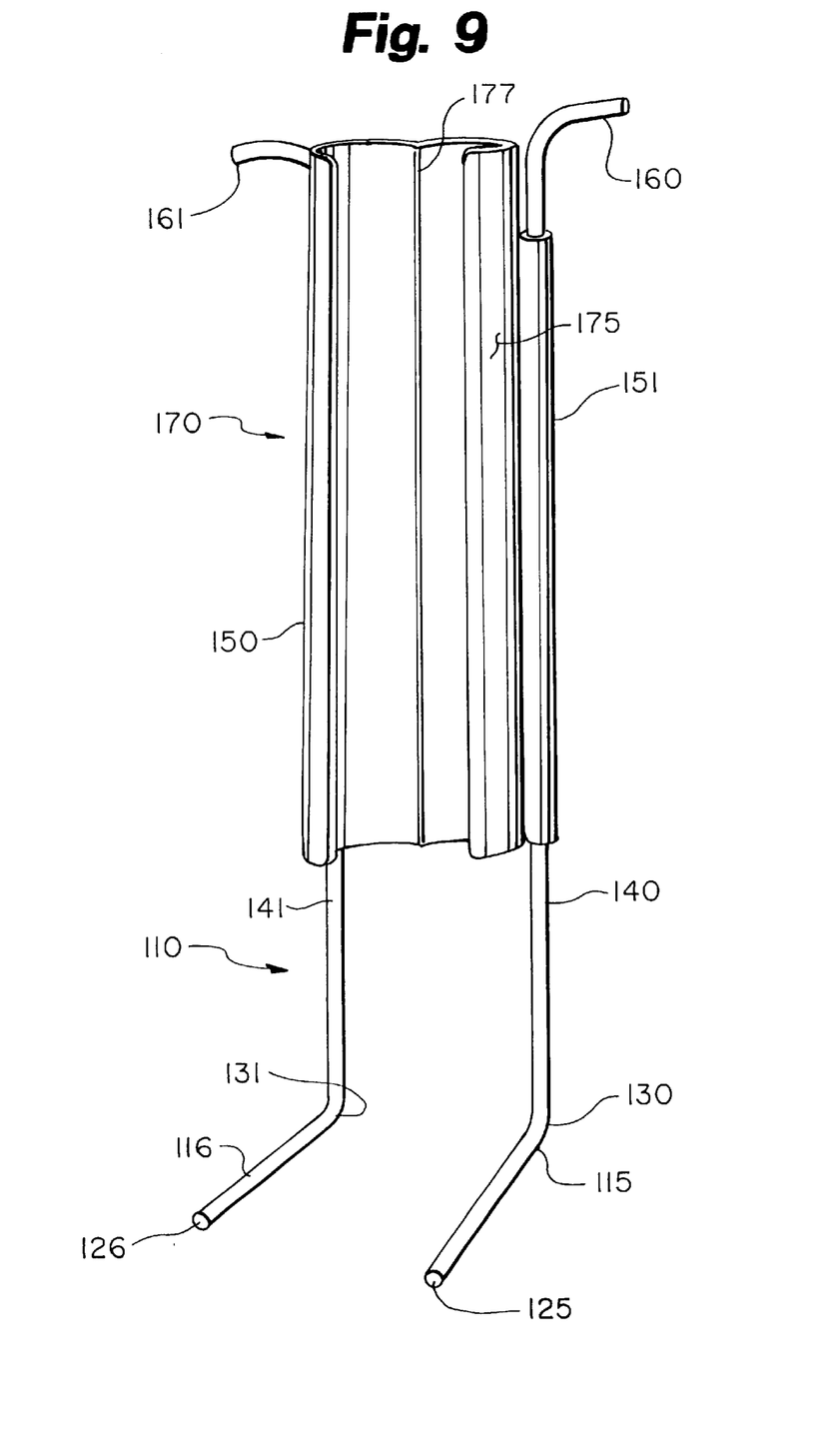
FIG. 9 is a perspective view, generally from the front, of a spacer support assembly for use in conjunction with the surgical instrument illustrated in FIG. 3.
Figure 10:
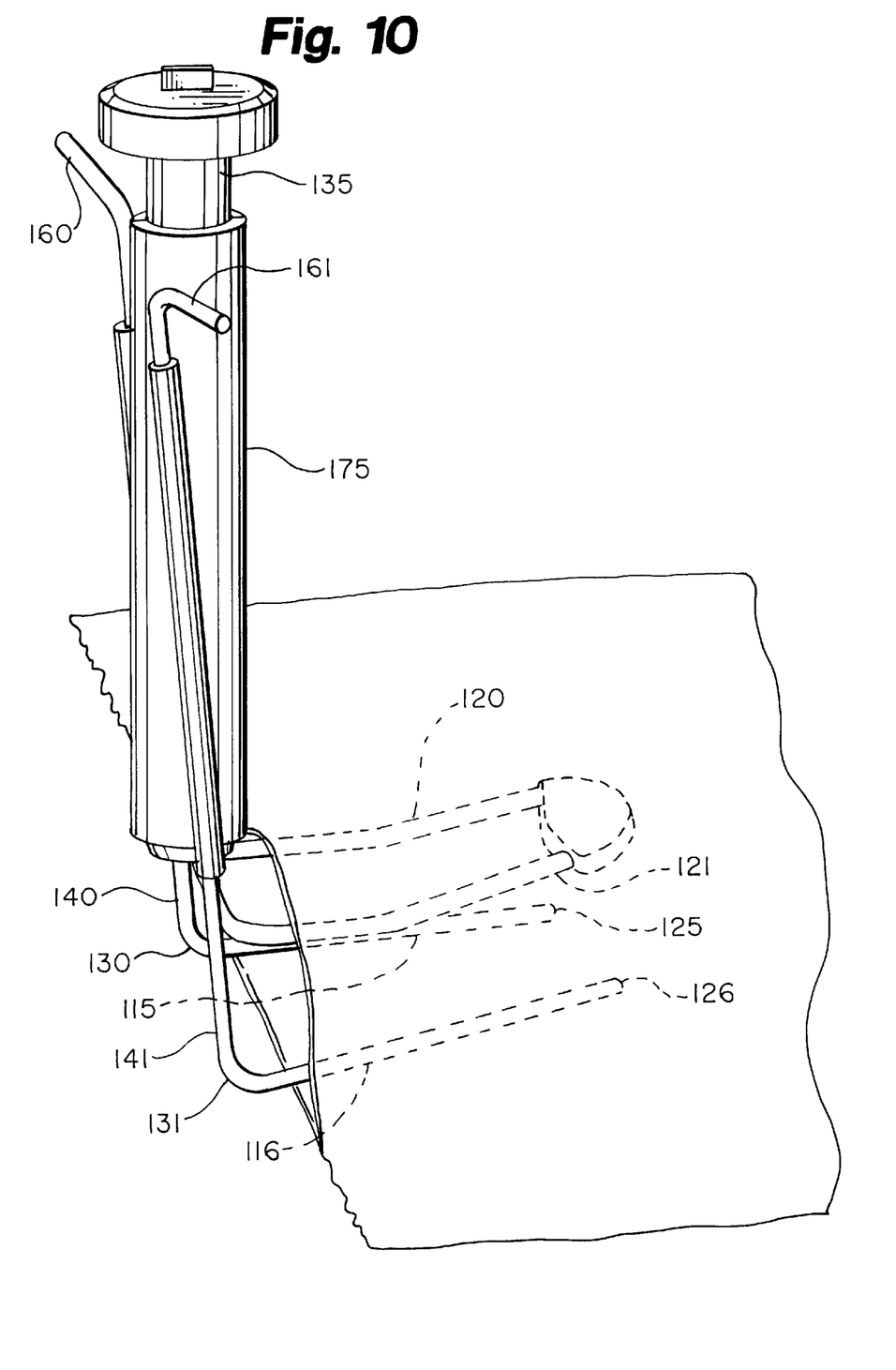
FIG. 10 is a perspective view, generally from the side, of the surgical instrument of FIG. 3 in use, with hidden portions under tissue indicated by dotted lines.

FIG. 6 illustrates another embodiment of a surgical instrument 200 according to the present invention. This embodiment is similar to the embodiments illustrated in FIGS. 1–5. The spacer arrangement 210 includes support feet or skis 211, 212 that extend from elongate extension members 240, 241 in a direction generally opposite of that in which the spacer limbs 215, 216 extend. The feet 211, 212 add to the stability of the device and aid in supporting the instrument when it is in position inside an incision.

Preferably, the web and light source arrangement is constructed to project light predominantly in the downward and forward directions. In this manner, the light that is projected onto the surgical area is maximized and the light projected onto surrounding areas is minimized. Further, by directing light forwardly, the user is not blinded by light shining rearwardly toward the use. The directional terms downwardly and forwardly as used herein relate to the orientation of the device as it is typically used in practice, though it should be understood that such terms are not intended to be limiting. More specifically, as illustrated in FIG. 7, the instrument has a reflective layer 310 adjacent a light source 315, such as a "grain of wheat" light, which is adjacent a window 317 through which the light shines. The reflective layer inhibits light from passing upwardly. In addition, a shaded area partially obstructs the rearward projection of light. Alternatively, as illustrated in FIG. 8, the web and light source arrangement is constructed with a light-refracting lens 350, such as a Fresnel lens, adjacent a light source 351.

In use, a surgeon performs an incision and isolates a saphenous vein with a Metzenbaum scissors, loop vein with elastic vessel loop. The surgeon then dissects the vein through proximal and distal incisions as far as visually possible using a Green Goiter. The surgeon then develops a tunnel using gentle digital dissection. Next, the lighted surgical instrument according to the present invention is inserted into the incision. In one preferred method, illustrated in FIG. 10, the blade limbs 120, 121 and the spacer limbs 115, 116 are all inserted into the incision or under the skin. In an alternate method, illustrated in FIG. 11, the blade limbs 120, 121 are inserted under the skin, while the spacer limbs 115, 116 engage the outside of the skin adjacent the incision. In this alternate method, the spacer limbs 115, 116 are preferably spread apart from one another such that they are not generally parallel, but rather form a truncated "V".

With the instrument inserted, the surgeon continues dissection allowing the surgical instrument according to the present invention to simultaneously illuminate and provide tunnel wall separation and retraction while using vessel loops for mobilization, medially and laterally. The surgeon locates side and perforating branches by slightly retracting the main saphenous vein.

In greater detail, the surgeon chooses a location for an initial incision to gain direct access to saphenous vein. After an incision is made and a vein located, a small spring retractor is used for skin retraction of the wound.

A Metzenbaum scissors (or similar tool) is used to dissect and isolate the vein from surrounding tissues. An elastic vessel band is then used to loop the vein enabling the surgeon to retract the vessel either laterally or medially by weighting the loop ends with a single small clamp. This, then, frees up both hands for continued dissection.

The surgeon then isolates the vein from surrounding tissues both proximally and distally within the incision as far as is possible without the aid of additional tissue retraction devices. The surgeon then inserts a "Green Goiter" retractor to facilitate the continued dissection in both directions within the wound. This tool provides good visualization for dissection as the tunnel is created but before additional light becomes necessary.

The surgeon then inserts a finger into the incision and begins to gently create a digitally guided tunnel adjacent to the course of the saphenous vein. The surgeon performs this maneuver in both directions from this single incision.

Next, the surgical instrument 100 according to the present invention is inserted into the digitally-created tunnel. It is held to obtain optimal lighting and for optimal retraction for further vein dissection. This process is repeated in the opposite direction.

The surgeon then uses curved Metzenbaum scissors or similar tool to isolate vessel side branches while using vessel loop to mobilize the vein in various directions as necessary. Once dissection has reached the point where vessel loops become less helpful and two hands would better facilitate dissection, spacer support arrangement 170 can be attached to the retractor and the spacer limbs 115, 116 deployed. This allows the retractor to stand alone using its own retraction technique to hold it securely in place within the tunnel.

Vein side branches can be double clipped with a clip applier while smaller ones can be separated by a bipolar cautery device. Branches that cannot easily be reached can wait until the conduit vessel is ready for removal from the tunnel.

Using a surgical instrument 100 according to the present invention, the surgeon identifiies the course of the saphenous vein under direct visualization to facilitate the positioning of the second incision. Once the second incision is made, the vein is retracted from the initial incision to help locate its exact position within the new incision. The surgeon then performs the dissection maneuvers described above with respect to the first incision, using a finger to carefully connect the vein tunnel in the second incision to the vein tunnel of the first incision.

After two or more incisions have been made to isolate the appropriate length of vein and both proximal and distal ends of the vein are severed, the double-clipped branches can now be cut between the clips or the unclipped branches can be separated with cautery scissors. The vein conduit is gently pulled from the tunnel with care being taken not to dislodge any clips in the process. With the conduit on the surgical field, preparation of the vein can be completed by clipping all side branches where necessary and checking carefully for any fluid leakage along the length of the vessel.

Although a preferred embodiment of the instrument has been shown there are a number of variations that should considered within the scope of the claims. For, example the members 26 and 28 are shown as solid wire forms but alternate cross section forms are practical including square and rectangular shapes. Tubular shape may be used as well. Although the inclusion of the power source in the handle is preferred for disposable versions of the device it should be clear that a remote power supply could be coupled to the handle via connector 36 to power the light source 22 from a remote supply (not shown). In a similar fashion the switch may take any conventional form or may be integrated into a remote power pack. The "bend" of the retractor blade 20 is acute with respect to the handle as indicated by angle A but other angular relationships are operable as well. For example the handle could be a reusable element with removable and disposable retractor blades temporally attached or coupled to the handle. The use of the members 26 and 28 as the conductors is preferred but separate wires may be used to deliver power to the light source 22.

What is claimed is:

1. A spacer support assembly for attachment to a surgical retractor having a handle and blade comprising:
   a) two spacer limbs;
   b) a jacket having a living hinge along its length to facilitate clamping of the jacket to the handle of the surgical retractor, said spacer limbs being coupled to said jacket suck that when said jacket is clamped to the retractor handle, said spacer limbs are generally parallel to the retractor blade.

2. A surgical instrument comprising:
   a handle having a distal end and a proximal end;
   a retractor blade member including a first fixed limb and a second fixed limb said member for insertion into a surgical wound, said retractor blade attached to said distal end of said handle, said retractor blade member extending in a direction away from said handle, whereby a view area axis is defined between said first and second limbs substantially parallel to the plane defined by said first and second limbs;
   a light source coupled to said retractor blade for illuminating said view area from a location near the most distal tip of the retractor blade;
   at least one conductor for coupling power to said retractor blade;
   first and second moveable spacer limbs coupled to said handle, said limbs extending generally parallel to and spaced from said first and second fixed limbs, and moveable in a direction away from said first and second fixed limbs remaining generally parallel to said first and second fixed limbs.

3. The instrument of claim 2, further comprising:
   a power source coupled to said handle.

4. The instrument of claim 2, further comprising:
   a switch coupled to said handle for controlling said light source.

5. The instrument of claim 2, further comprising:
   one or more batteries located within said handle forming a power source for said light source.

6. The instrument of claim 1 wherein said retractor blade comprises:
 a first electrically conductive member forming said first fixed limb;
 a second electrically conductive member forming said second fixed limb;
 said first and second members electrically isolated from each other and each coupled to said light source for conducting power to said light source.

7. The instrument of claim 6, further comprising:
 a web coupled to said retractor blade for positioning said light source.

8. The instrument of claim 2, further comprising:
 a remote power source for connection to said handle, for powering said light source.

9. A surgical instrument according to claim 2, further comprising:
 spacer adjusting means coupled to said handle and to said moveable spacer limbs for selectively varying the space between said spacer limbs and said first and second fixed limbs.

10. A surgical instrument according to claim 2, wherein said spacer limbs are slidably coupled to said handle such that each of said spacer limbs can be selectively positioned to achieve the desired space between the moveable spacer limbs and the first and second fixed limbs.

11. A surgical instrument according to claim 10, wherein said spacer limbs are independently slidable with respect to said handle.

12. A surgical instrument according to claim 10, wherein said spacer limbs are coupled to flanges that extend generally perpendicular to said handle, said flanges positioned adjacent said proximal end of said handle.

13. A surgical instrument according to claim 12, wherein each said spacer limbs is integrally connected to each one of said flanges, said handle having coupled thereto elongate tubes extending lengthwise along the handle, and each said elongate member positioned within one said tube, said respective flange and said respective spacer limb being outside of said tube.

14. A surgical instrument according to claim 13, wherein each of said elongate flanges is disposed at an angle to said elongate member, such that said elongate member's movement in a direction toward the distal end is limited by the flange abutting the proximal end of said tube.

15. A surgical instrument according to claim 2, wherein said spacer limbs are removably coupled to said handle.

16. A surgical instrument according to claim 2, wherein said spacer limbs are spaced a distance of between zero inches and 2.5 inches from the plane defined by said first and second limbs.

17. A surgical instrument according to claim 16, wherein said spacer limbs are spaced a distance of about 1 inch from the plane defined by said first and second limbs.

18. A method of dissecting saphenous vein comprising the steps of:
 a) providing a surgical instrument having:
  (i) a handle having a distal end and a proximal end;
  (ii) a retractor blade member including a first fixed limb and a second fixed limb said member for insertion into a surgical wound, said retractor blade attached to said distal end of said handle, said retractor blade member extending in a direction away from said handle, whereby a view area axis is defined between said first and second limbs substantially parallel to the plane defined by said first and second limbs;
  (iii) a light source coupled to said retractor blade for illuminating said view area;
  (iv) at least one conductor for coupling power to said retractor blade; said light source coupled to said retractor blade;
  (v) first and second moveable spacer limbs coupled to said handle, said limbs extending generally parallel to and spaced from said first and second limbs;
 b) making an incision in a patient's skin;
 c) inserting said blade of said instrument into said incision to retract tissue away from a vein to be dissected and maintaining a tunnel surrounding the vein; and
 d) dissecting the vein.

* * * * *